United States Patent [19]

Parsons

[11] Patent Number: 5,505,094
[45] Date of Patent: Apr. 9, 1996

[54] TEST BLOCK FOR HANDCUFF KEY AND METHOD OF USING SAME

[75] Inventor: Kevin L. Parsons, Appleton, Wis.

[73] Assignee: Armament Systems and Procedures, Inc., Appleton, Wis.

[21] Appl. No.: 385,100

[22] Filed: Feb. 7, 1995

[51] Int. Cl.[6] .................................................. G01N 3/20
[52] U.S. Cl. ............................................ 73/849; 73/788
[58] Field of Search ........................... 73/788, 849, 853, 73/854; 70/403, 454, 460

[56] References Cited

U.S. PATENT DOCUMENTS

| | | | |
|---|---|---|---|
| 723,549 | 3/1903 | Roche | 70/403 |
| 790,091 | 5/1905 | Turner | 70/403 |
| 875,965 | 1/1908 | Svensen | 70/403 |
| 2,859,613 | 4/1956 | Green | 73/849 |
| 4,426,179 | 1/1984 | Jefferson | 73/865.9 |
| 5,022,273 | 6/1991 | Evans | 73/849 |

*Primary Examiner*—Richard Chilcot
*Assistant Examiner*—Max Noori
*Attorney, Agent, or Firm*—Robert C. Curfiss; Butler & Binion

[57] ABSTRACT

A test block and method of testing for law enforcement personnel to quickly and easily test the strength of and gauge the dimensions of a handcuff key before it is used in actual handcuffs. The block has an opening in its center which receives the latch tab end of the key and also serves as a gauge for the maximum permissible dimensions of a handcuff key. To test the key, the officer inserts the latch tab end in the opening and exerts pressure on the key with his thumb while holding the block in a stable position. The test block has a thickness which is sufficient to hold the key in the test block as it is being tested.

9 Claims, 1 Drawing Sheet

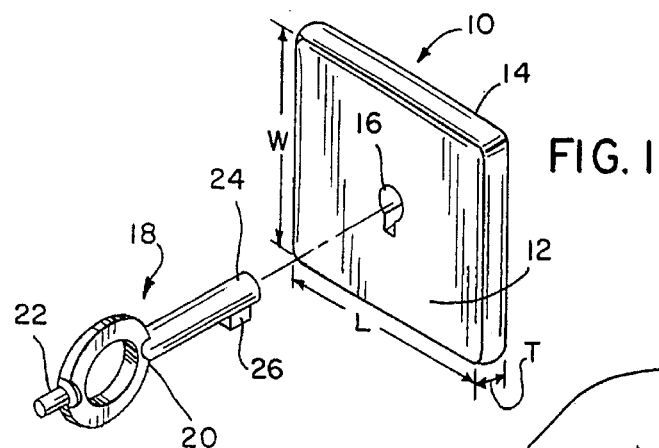
FIG. 1
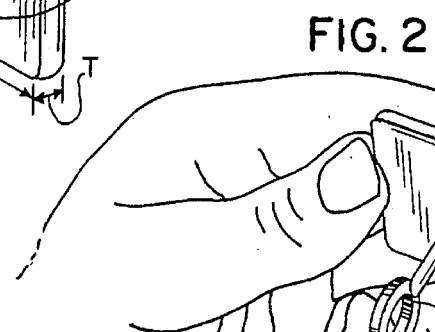
FIG. 2
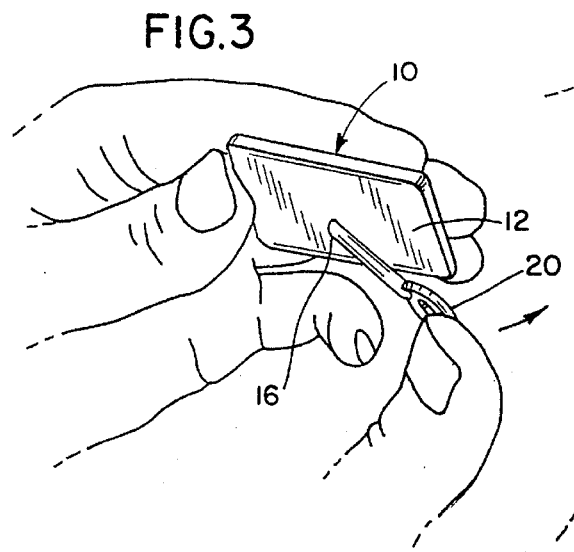
FIG. 3
FIG. 4
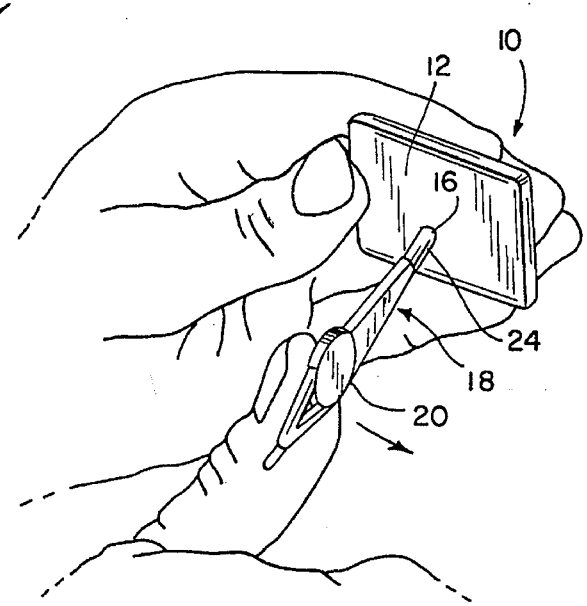
FIG. 5

TEST BLOCK FOR HANDCUFF KEY AND METHOD OF USING SAME

BACKGROUND OF INVENTION

1. Field of Invention

The invention is generally related to a method and apparatus for testing by law enforcement personnel and is specifically directed to a handcuff key test block and a method for testing the strength of a key using the test block.

2. Description of the Prior Art

Handcuffs and handcuff keys are an important part of the official issue equipment for law enforcement personnel. Generally, a standard handcuff key carried by law enforcement personnel has an "L" shaped key body with a rectangular latch at one end and a locking pin at the opposite end and can be used to unlock any set of standard handcuffs. Typically, handcuffs unlock by first turning the key in one direction to release the double locking mechanism and then turning the key in the opposite direction to release the locking mechanism. Once handcuffs are applied, they will continue to rachet shut. Thus, the pin is used to set the double lock in place. This two step process increases the security of handcuff restraining devices.

While a standard handcuff key should work with all standard handcuffs, there are some keys which are of inferior quality and hence, either do not fit or are not strong enough to unlock the handcuffs. Such keys may bend or break when an officer attempts to unlock handcuffs using the key. If the key breaks off or bends so that it cannot be removed, the handcuffs then have to be cut off with bolt cutters and are destroyed. Because handcuffs are expensive, law enforcement personnel need a way to test a key before placing in use to assure that it will operate in the intended manner.

Therefore, there is a need for an inexpensive, convenient testing apparatus and method for quickly and testing a handcuff key before it is used in the actual handcuffs.

SUMMARY OF THE INVENTION

The subject invention is directed to a test block and a method of using the test block to test handcuff keys before they are used. The invention is a test block into which a handcuff key is inserted and pressure is applied. The block is a testing tool which is easily carried by law enforcement personnel and can be conveniently used to quickly and easily conduct tests in any setting.

The test block of the subject invention includes a key hole which also serves as a gauge for the maximum permissible dimensions of a handcuff key. If a key will not fit into the key hole, the officer is alerted that the key may not fit some duty handcuffs. The block has a thickness which is sufficient to hold the key in a upright position after it is inserted into the key hole and engages the key while it is being tested.

The test block permits a law enforcement officer to quickly and easily test the strength of a handcuff key before inserting the key into the actual handcuffs. To test the key, the officer inserts the key into the hole and exerts pressure on the key with his thumb. An inferior key will bend when tested so that by conducting the test, the officer avoids breaking the key in the handcuffs, resulting in loss of the handcuffs at substantial expense. A "good" key will not bend when tested and is safe to use.

Therefore, it is an object and feature of the subject invention to provide a means and method for assuring the size and desirability of a standard handcuff key.

It is an additional object and feature of the subject invention to provide a test block for testing the strength of a handcuff key before using the key in the actual handcuffs.

It is another object and feature of the subject invention to provide a method of testing the strength of a handcuff key before using the key in the actual handcuffs.

It is a further object and feature of the subject invention to provide a test block and method for gauging the maximum permissible dimensions of a handcuff key.

Other objects and features will be readily apparent from the accompanying drawings and description.

BRIEF DESCRIPTION OF THE DRAWINGS

FIG. 1 is a perspective view of the test block and handcuff key before the key is inserted into the opening in the block.

FIG. 2 is a perspective view of the test block and handcuff key inserted into the test block showing the method of testing the key by applying pressure to the key inserted in the test block as the block is held in a stable position.

FIG. 3 is a perspective view of the test block and handcuff key inserted into the block showing how an inferior key is bent when tested by applying pressure to the key.

FIG. 4 is an enlarged cross-sectional view of the test block opening and handcuff key inserted into the opening showing the bent key after pressure has been applied.

FIG. 5 is a perspective view of the test block and handcuff key inserted into the block showing how a satisfactory key does not bend when tested using the test block.

DETAILED DESCRIPTION OF THE DRAWINGS

The preferred embodiment of the test block of the subject invention is shown in FIG. 1 and is designated by the numeral 10. The test block 10 permits law enforcement personnel to quickly and easily test handcuff keys in any setting before using them in actual handcuffs.

The test block 10 is rigid, and is typically made of a hardened material such as steel or the like. The block has a top surface 12 and a bottom surface 14. The top surface 12 includes an opening 16 which is positioned in the center of the block and is adapted to receive a handcuff key 18. In the preferred embodiment, the top and bottom surfaces 12 and 14 of the rigid test block 10 are flat. The opening 16 may extend through the block or have a closed bottom, as desired.

As shown in FIGS. 1 and 2, the handcuff key 18, having a key body 20 with opposite ends 22, 24 and a flat, rectangular latch tab 26 extending from one end 24, is inserted into the opening 16. The opening 16 is sized to receive the latch tab end 24 of the handcuff key 18. In the preferred embodiment, the opening 16 is specifically configured to receive only handcuff keys which are properly dimensioned to unlock standard issue handcuffs and function as a "Go/No Go" gauge. If a key will not fit into the opening 16 of the test block 10, an officer is alerted that the key may not fit some duty handcuffs. Thus, the test block 10 serves as a gauge for determining the maximum permissible dimensions of a handcuff key.

As shown, the test block 10 is rectangular having a length L, a width W and the thickness T. However, the test block 10 may be any desired shape provided that the opening 16 is substantially in the center of the test block and the block has the thickness T. In the preferred embodiment, the rigid test block 10 is constructed of hardened steel and has a thickness T of 3/16 inches. The overall dimensions of the block are 1.5 inches×1.5 inches square. This is sufficient to provide leverage while the testing is conducted. In addition, the thickness T is sufficient to hold the key in an upright position once the key is inserted into the opening 16.

To test a handcuff key using the test block 10, the latch tab end 24 of the handcuff key 18 is inserted into the opening 16. After the key is inserted, the test block 10 is held in a stable position and pressure is applied to the key body 20 (see FIGS. 2, 3 and 5). In the preferred embodiment, the test block 10 may be placed on a flat surface and held in place with one hand while the officer exerts pressure on the key body 20, in either direction, with the thumb of the other hand. Also, the block may be held as shown in FIGS. 2 and 3 to perform the test.

As shown in FIG. 3, an inferior key which is not sufficiently strong will bend when tested and pressure is applied to the key body 20. Thus, by conducting the test using the test block 10, an officer avoids potentially breaking the key in the actual handcuffs. As shown in FIG. 5, a key which is sufficiently strong, will not bend when tested. Thus, by using the test block 10, an officer determines that the key is safe to use in the actual handcuffs.

While specific embodiments and features of the invention have been disclosed herein, it will be readily understood that the invention encompasses all enhancements and modifications within the scope and spirit of the following claims.

What is claimed is:

1. A method for testing a handcuff key for field use by law enforcement personnel, the key having a substantially axial key body with opposite ends and a flat, rectangular latch tab extending from one end for releasing a handcuff lock, the method comprising the steps of:
   a. providing a portable, rigid test block having a predetermined thickness and including an opening for receiving the latch tab end of the handcuff key;
   b. inserting the latch tab end of the handcuff key to be tested into the opening whereby the inserted key is positioned perpendicular to the test block;
   c. holding the test block in a stable position and applying radial pressure to the key body of the handcuff key; and
   d. removing the handcuff key from the test block.

2. The method of claim 1, the holding step further comprising placing the test block on a flat surface and exerting the pressure on the key body with the thumb.

3. The method of claim 1, wherein the opening is precisely dimensioned to receive a standard duty handcuff key and function as a "Go", "No Go" gauge.

4. A method for testing a handcuff key for field use by law enforcement personnel, the key having a substantially axial key body with opposite ends and a flat, rectangular latch tab extending from one end for releasing a handcuff lock, the method comprising the steps of:
   a. providing a portable, rigid test block having a predetermined certain thickness and including an opening for receiving the latch tab end of the handcuff key, said opening being sized to receive a handcuff key having dimensions which fit the lock of standard issue handcuffs; and
   b. attempting to insert the latch tab end of the handcuff key to be tested into the opening for determining whether the handcuff key is dimensioned to fit the lock of standard issue handcuffs.

5. A method for testing the strength and gauging the dimensions of a handcuff key for field use by law enforcement personnel, the key having a substantially axial key body with opposite ends and a flat, rectangular latch tab extending from one end for releasing a handcuff lock, the method comprising the steps of:
   a. providing a portable, rigid test block having a predetermined thickness and including an opening of predetermined dimension for receiving the latch tab end of the handcuff key, said opening being sized to receive a handcuff key having dimensions which fit the lock of standard issue handcuffs;
   b. attempting to insert the latch tab end of the handcuff key to be tested into the opening for determining whether the handcuff key is dimensioned to fit the lock of standard issue handcuffs;
   c. holding the test block in a stable position and applying radial pressure to the key body of the handcuff key which has been inserted into the block for determining whether the handcuff key is satisfactory or is inferior and will bend or break when pressure is applied; and
   d. removing the handcuff key from the block after the determination has been made.

6. A portable test device for testing a handcuff key for field use by law enforcement personnel, the key having a substantially axial key body with opposite ends and a flat, rectangular latch tab extending from one end for releasing a handcuff lock, the device comprising:
   a. a portable test block having a center, a top and bottom surface and a predetermined thickness;
   b. an opening of predetermined size in the center of the top surface of the test block, said opening extending into the block and sized to receive the latch tab end of the handcuff key, whereby the handcuff key may be inserted into the opening and pressure applied to determine whether the key will bend or break.

7. The device of claim 6, wherein the test block is constructed of hardened steel.

8. The device of claim 7, wherein the test block has a length of 1.5 inches, a width of 1.5 inches and a thickness of 3/16 inches.

9. The device of claim 6, wherein the opening is specifically configured to receive a key for unlocking standard issue handcuffs for determining whether the tested key is correctly dimensioned to fit the lock of standard issue handcuffs.

* * * * *